(12) United States Patent
Min et al.

(10) Patent No.: US 11,618,895 B2
(45) Date of Patent: Apr. 4, 2023

(54) METHOD FOR EXTRACTING NUCLEIC ACIDS FROM BIOLOGICAL SAMPLE

(71) Applicant: CT BIO CO., LTD, Seoul (KR)

(72) Inventors: Jun Hong Min, Seongnam-si (KR); Chang Yoon Baek, Seoul (KR)

(73) Assignee: CT BIO CO., LTD, Seoul (KR)

( * ) Notice: Subject to any disclaimer, the term of this patent is extended or adjusted under 35 U.S.C. 154(b) by 149 days.

(21) Appl. No.: 16/111,761

(22) Filed: Aug. 24, 2018

(65) Prior Publication Data

US 2019/0055541 A1 Feb. 21, 2019

Related U.S. Application Data

(63) Continuation-in-part of application No. PCT/KR2017/002088, filed on Feb. 24, 2017.

(30) Foreign Application Priority Data

Feb. 26, 2016 (KR) .................. 10-2016-0023251
Feb. 21, 2017 (KR) .................. 10-2017-0023193

(51) Int. Cl.
| | | |
|---|---|---|
| *C12N 15/10* | (2006.01) | |
| *C12N 1/06* | (2006.01) | |
| *C12N 13/00* | (2006.01) | |
| C12Q 1/6806 | (2018.01) | |

(52) U.S. Cl.
CPC ......... *C12N 15/1003* (2013.01); *C12N 1/066* (2013.01); *C12N 13/00* (2013.01); *C12N 15/10* (2013.01); *C12N 15/1017* (2013.01); *C12N 2509/10* (2013.01); *C12N 2523/00* (2013.01); *C12Q 1/6806* (2013.01)

(58) Field of Classification Search
CPC ............... C12N 15/1003; C12N 15/10; C12N 15/1017; C12N 1/066; C12N 13/00; C12N 2509/10; C12N 2523/00; C12Q 1/6806; C12Q 2523/32; C12Q 2523/305
See application file for complete search history.

(56) References Cited

U.S. PATENT DOCUMENTS

| | | | |
|---|---|---|---|
| 2006/0019379 A1 | 1/2006 | Taylor et al. | |
| 2007/0238109 A1* | 10/2007 | Min ................. | C12N 15/1006 435/6.15 |
| 2009/0131649 A1 | 5/2009 | Lee et al. | |
| 2012/0058094 A1* | 3/2012 | Blaser ............... | A61K 9/0053 424/93.41 |
| 2012/0129921 A1* | 5/2012 | Ledent .............. | C12N 15/1003 514/44 R |
| 2014/0212868 A1* | 7/2014 | Wilmes .............. | C12N 1/066 435/6.1 |

FOREIGN PATENT DOCUMENTS

| | | | |
|---|---|---|---|
| CN | 101333523 A | 12/2008 | |
| JP | 2005510239 A | 4/2005 | |
| KR | 10-2009-0050748 A | 12/2014 | |
| KR | 10-2014-0140317 A | 12/2014 | |
| WO | WO-2015154013 A1 * | 10/2015 | ........... C12N 15/101 |

OTHER PUBLICATIONS

Claassen, S et al. A comparison of the efficiency of five different commercial DNA extraction kits forextraction of DNA from faecal samples. Journal of Microbiological Methods. 2013. 94: 103-110. (Year: 2013).*
Quigley, L et al. A comparison of methods used to extract bacterial DNA from raw milk and raw milk cheese. Journal of Applied Microbiology. 2012. 113: 96-105. (Year: 2012).*
Wesolowska-Andersen, A et al. Choice of bacterial DNA extraction method from fecal material influences community structure as evaluated by metagenoic analysis. Microbiome. 2014. 2:19. 11 pages. (Year: 2014).*
Kav, AB et al. A method for purifying high quality and high yield plasmid DNA for metagenomic and deep sequencing approaches. Journal of Microbiological Methods. 2013. 95: 272-279. (Year: 2013).*
Eon-Duval, A et al. Precipitation of RNA impurities with high salt in a plasmid DNA purification process: use of experimental design to determine reaction conditions. Biotechnology and Bioengineering. 2003. 83(5): 544-553. (Year: 2003).*
Li, N et al. High-performance of deep eutectic solvent based aqueous bi-phasic systems for the extraction of DNA. RSC Advances. 2016. 6: 84406-84414. First published Aug. 31, 2016. (Year: 2016).*
Yu et al., Biotechniques, vol. 36, No. 5, pp. 808-813 (2004).
Whitney et al., The Journal of Molecular Diagnostics, vol. 6, No. 4, pp. 386-395 (2004).
Hill et al., Pathogens, vol. 4, pp. 335-354 (2015).
Bolano et al., FEMS Yeast Research, vol. 1, pp. 221-224 (2001).
PCT International Search Report and Written Opinion dated Jun. 12, 2017 from corresponding Application No. PCT/KR2017/002088, 11 pages.

(Continued)

*Primary Examiner* — Renee Claytor
*Assistant Examiner* — Susan E. Fernandez
(74) *Attorney, Agent, or Firm* — Dilworth IP, LLC

(57) ABSTRACT

The present invention relates to a method for extracting nucleic acids from a biological sample, and the extraction method presents a novel method for effectively extracting nucleic acids. When nucleic acids are extracted from biological samples in the related art, various impurities present in the biological samples are not properly removed, such that the purification rate is low, but the present invention provides a method for extracting nucleic acids from a biological sample of which the bacteria, virus and nucleic acid recovery rates are enhanced, by adding a surfactant and a sodium sulfate ($Na_2SO_4$) solution in a biological sample disruption step and a purification step, thereby enabling pathogens to be detected more sensitively and accurately.

10 Claims, 12 Drawing Sheets

(56) References Cited

OTHER PUBLICATIONS

K. Lemarchand et al., "Optimization of Microbial DNA Extraction and Purification from Raw Wastewater Samples for Downstream Pathogen Detection by Microarrays", J. Microbiol. Methods, 2005年, vol. 63, p. 115-126.

S. Claassen et al., "A Comparison of the Efficiency of Five Different Commercial DNA Extraction Kits for Extraction of DNA from Faecal Samples", J. Microbiol. Methods, 2013年, vol. 94, p. 103-110.

1st Office Action from JPO in Application No. JP 2018-562493, dated Jul. 8, 2019. 7 pages.

Yeates C et al: "Methods for microbial DNA extraction from soil for PCR amplification", Biological Procedures Online, vol. 1, No. 1, pp. 40-47 p. 41, 2nd para.

Hans-Olof Johansson et al: Plasmid DNA partitioning and separation using poly(ethylene glycol)/poly(acrylate)/salt aqueous two-phase systems, Journal of Chrmatography A, vol. 1233, pp. 30-35 p. 31-12, para. 2.2.7; fig. 4.

Kageyama K et al: "Refined PCR Protocol for detection of plant pathogens in soil", Journal of General Plant Pathology, Phytopathological Society of Japan, Tokyo, vol. 69, No. 3, pp. 153-160 Fig. 1.

1st Office Action from EPO in Application No. 17756869.8, dated Jul. 4, 2019. 10 pages.

Communication under Rule 71(3) EPC, Intention to grant, in related European Patent Application No. 17756869.8; dated Oct. 27, 2021, 34 pages.

Instructions to the Communication pursuant to Rule 71(3) EPC, in related European Patent Application No. 17756869.8, 1 page.

Zhongtang, Yu, et al., "Improved extraction of PCR-quality community DNA from digesta and fecal samples", Biotechniques Rapid Dispatches, US, vol. 36, No. 5, doi:10.2144/04365ST04, ISSN 0736-6205, pp. 808-812, May 1, 2004.

\* cited by examiner

FIG. 3A
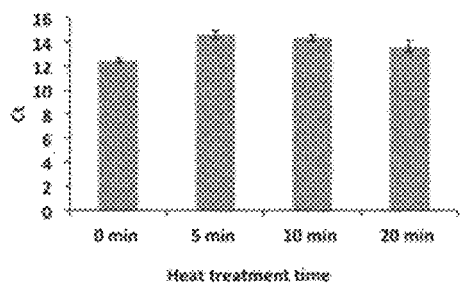
FIG. 3C
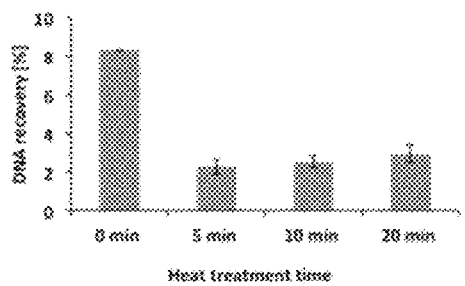
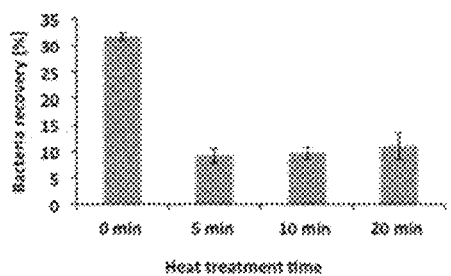
FIG. 3B
FIG. 4A
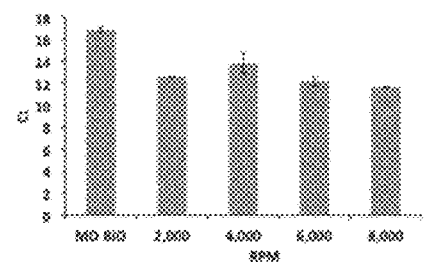
FIG. 4C
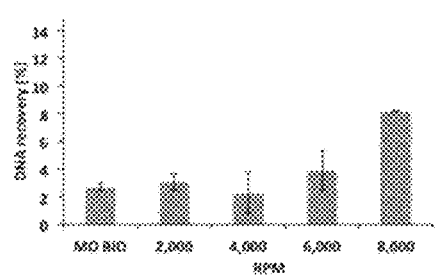
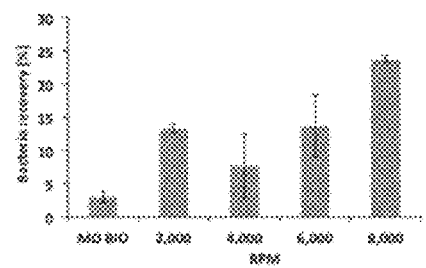
FIG. 4B
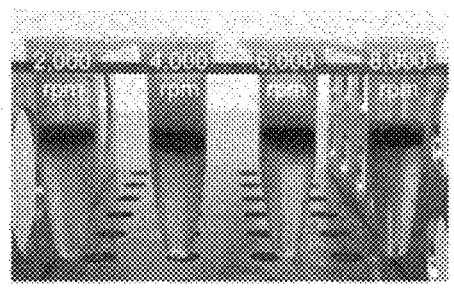
FIG. 4D FIG. 5A
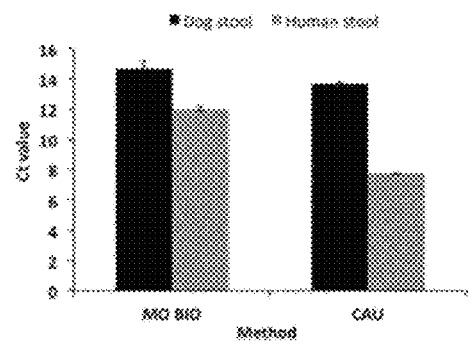
FIG. 5C
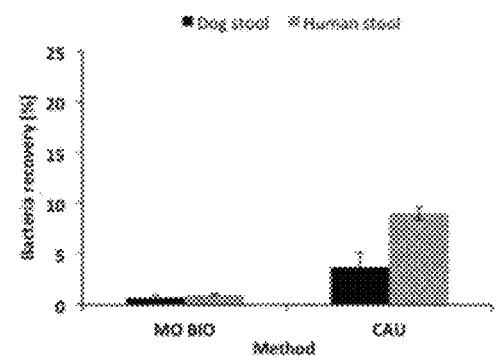
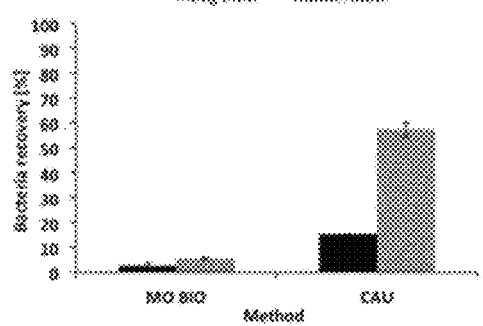
FIG. 5B
FIG. 6
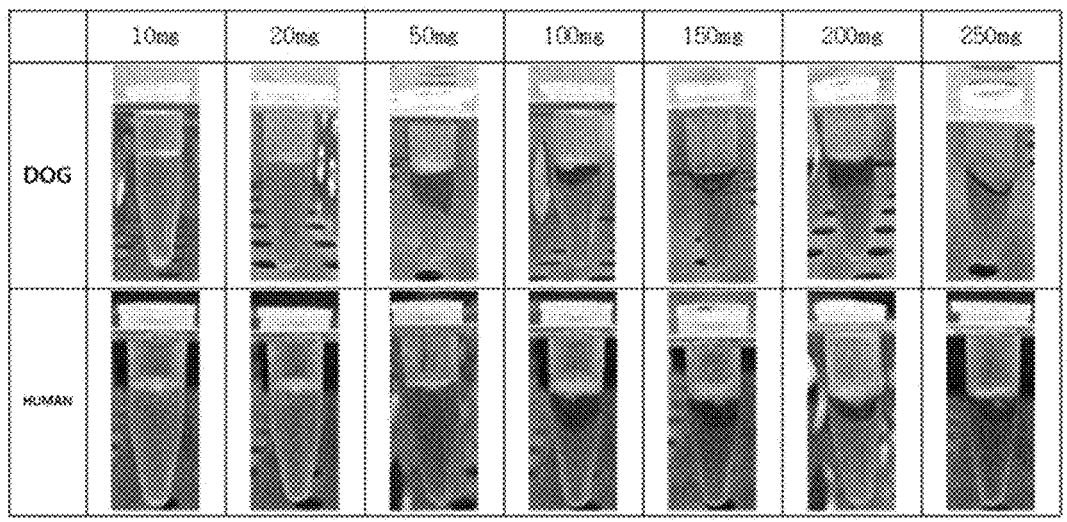

FIG. 7A
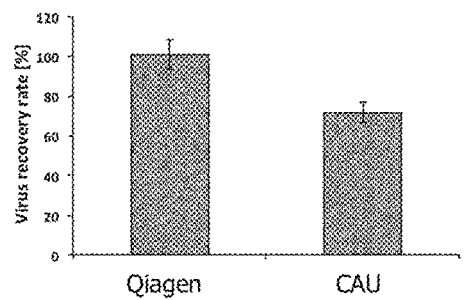
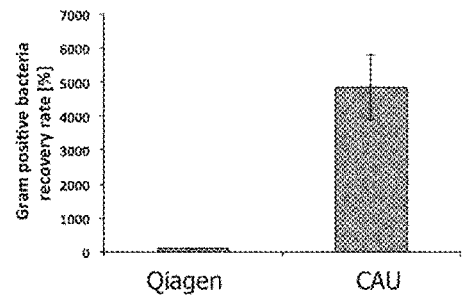
FIG. 7B

FIG. 8A
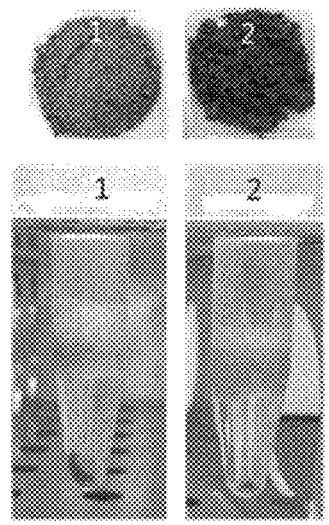
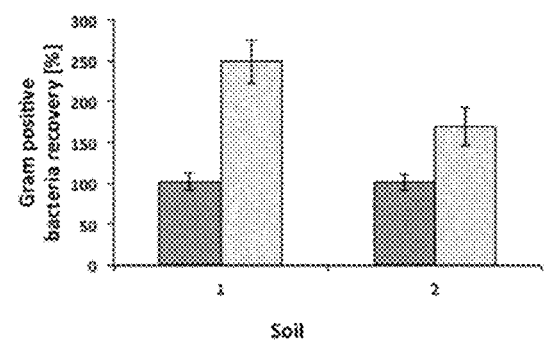
FIG. 8B

METHOD FOR EXTRACTING NUCLEIC ACIDS FROM BIOLOGICAL SAMPLE

The present invention provides a method for extracting nucleic acids from a biological sample, and more particularly, to a method for extracting nucleic acids, which improves the nucleic acid recovery rate by effectively removing impurities from complex environments and biological samples by a method which is differentiated from existing commercial methods for extracting nucleic acids using biological samples.

BACKGROUND

Recently, various methods which detect pathogens sensitively and accurately have been developed, such as a selective media method, a specific reaction method using specific antibody or antigen, or a nucleic acid amplification method. The detection limits of the aforementioned methods have been rapidly developed by introducing the amplification of detection signals using several biological or chemical materials such as a nano particle, an enzyme, a chemiluminescent reagent, or a liposome, and among them, several methods have already been commercialized.

However, since the sample pretreatment process (concentration and purification) continues to require a long period of time, the development of a signal amplification method and shortening of the detection time still remain as important development tasks in the pathogen detection method from a sample.

It is difficult to perform biological detection methods such as assays using antibodies or enzymatic reactions without a pretreatment process due to complex components of a sample, and furthermore, it is difficult to apply the concentration process to a target that cannot be cultured, such as the norovirus.

Physical, chemical or biological concentration methods of pathogens inherent in drinking water and simple food samples such as fruits and vegetables have been developed variously, such as a centrifuge method, a deposition method using polyethylene glycol (PEG), a concentration method using a charged filter, an adsorption method through an increase in ion intensity using NaCl, a concentration method using a divalent cation ($Ca^{2+}$ and $Mg^{2+}$), and a separation method using antibodies.

However, there remain two important problems of shortening the pretreatment time and increasing the detection efficiency at low concentration in order to quickly and productively detect bacteria or viruses on site. Therefore, there is a continuous need for a method for simply concentrating and destroying pathogens from the scientific or commercial viewpoint.

When a biological sample is stool, as an existing commercialized process, a method for precipitating the stool and separating nucleic acids from the stool has been frequently used during the process of separating the stool sample. For example, MoBio Laboratories Inc. (Carlsbad, USA) suggests a method of flocculating impurities by using a trivalent cation such as aluminum, and an important characteristic in concentrating/purifying DNA by using the Boom technology lies in a method for precipitating impurities by using $Al^{3+}$ and $NH_4^{3+}$, and the like, and the method is very effective for a complex sample such as stool or soil and shows the highest efficiency among the existing technologies, but the recovery rate thereof is only less than 1%. Qiagen, Inc. (Hilden, Germany) suggests a method of adsorbing and removing a material inhibiting the polymerase chain reaction (PCR) by using a carbohydrate-based adsorptive matrix, but this method is very effective for purifying a complex sample such as a stool sample, but the recovery rate thereof is less than 0.1%. Further, Zymo Research Corp. (Irvine, USA) proposes a method for extracting nucleic acids present in stool by applying physical forces using 500 μm beads, but has a limit in that the purification rate thereof is low due to the failure to remove various impurities present in the stool sample.

Therefore, there is a need for developing a method capable of increasing the nucleic acid extraction rate by removing various impurities present in the complex sample such as stool.

SUMMARY OF THE INVENTION

The present invention provides a method for extracting nucleic acids from a biological sample, which is capable of improving the recovery rates of bacteria, virus and nucleic acids by using a surfactant and kosmotropic salt in order to effectively extract nucleic acids from the biological sample.

An aspect of the present invention provides a method for extracting nucleic acids from a biological sample, the method including: (a) disrupting a biological sample by bead-beating a biological sample-bead solution prepared by adding a buffer solution, a surfactant, and beads to the biological sample; (b) separating the disrupted biological sample-bead solution; (c) performing a repurification by adding a kosmotropic salt solution to the purified solution; and (d) extracting nucleic acids from the repurified solution.

According to an exemplary embodiment of the present invention, the surfactant may be an anionic surfactant.

According to an exemplary embodiment of the present invention, the surfactant may be present in an amount of 1 to 20% (v/v) based on a total weight of the biological sample.

According to an exemplary embodiment of the present invention, step (a) may be disrupting the biological sample by bead-beating the biological sample-bead solution under a condition of 10 to 80 Hz.

According to an exemplary embodiment of the present invention, the purification may be carried out through centrifugation or filtration.

According to an exemplary embodiment of the present invention, the repurification may be carried out through centrifugation or a heat treatment. According to an exemplary embodiment of the present invention, the heat treatment may be carried out at 50 to 90° C.

According to an exemplary embodiment of the present invention, the kosmotropic salt solution may be a sodium sulfate ($Na_2SO_4$) solution.

According to an exemplary embodiment of the present invention, the kosmotropic salt solution may be a 1.0 to 5.0 M solution.

According to an exemplary embodiment of the present invention, the biological sample may be any one selected from the group consisting of stool, blood, and soil.

An aspect of the present invention provides a method for extracting nucleic acids from a biological sample, the method including: (a) disrupting a biological sample by bead-beating a biological sample-bead solution prepared by adding a buffer solution, a surfactant, and beads to the biological sample; (b) centrifuging and purifying a biological sample-bead solution in which the biological sample is disrupted; (c) performing a repurification by adding a kosmotropic salt solution to the purified solution and centrifuging the resulting mixture; and (d) extracting nucleic acids from the repurified solution.

Another aspect of the present invention provides a method for extracting nucleic acids from a biological sample, the method including: (a) disrupting a biological sample by bead-beating a biological sample-bead solution prepared by adding a buffer solution, a surfactant, and beads to the biological sample; (b) filtering and purifying a biological sample-bead solution in which the biological sample is disrupted; (c) performing a repurification by adding a kosmotropic salt solution to the purified solution and performing a heat treatment; and (d) extracting nucleic acids from the repurified solution.

According to the present invention, impurities in the sample are effectively removed by adding a surfactant and a kosmotropic salt solution in the disrupting of the biological sample and the purifying of the biological sample, respectively, thereby improving the recovery rates of bacteria, virus and nucleic acids and exhibiting an effect of enabling pathogens to be detected more sensitively and accurately.

BRIEF DESCRIPTION OF DRAWINGS

FIGS. 3A-3C illustrate the total bacteria recovery (FIG. 3A), the bacteria recovery rate (FIG. 3B), and the nucleic acid recovery rate (FIG. 3C) according to the heat treatment.

FIGS. 4A-4D illustrate the total bacteria recovery (FIG. 4A), the bacteria recovery rate (FIG. 4B), the nucleic acid recovery rate (FIG. 4C), and the stool separation (FIG. 4D) according to the intensity of centrifugation.

FIGS. 5A-5C illustrate the total bacteria recovery (FIG. 5A), the bacteria recovery rate (FIG. 5B), and the nucleic acid recovery rate (FIG. 5C) according to the type of stool sample.

FIG. 6 illustrates the separation and purification results of dog (top) and human (bottom) stool samples according to the amount of the stool sample.

FIGS. 7A-7B illustrate the separation and purification results of a human blood sample according to the amount of the sample (FIG. 7A), virus recovery rates and Gram positive bacteria recovery rates (FIG. 7B) according to the present invention and a commercially-available kit (Qiagen, Inc.).

FIGS. 8A-8B illustrate the separation and purification results of soil samples (FIG. 8A), and Gram positive bacteria recovery rates in the soil samples (FIG. 8B).

DETAILED DESCRIPTION OF THE INVENTION

Figure 1A:
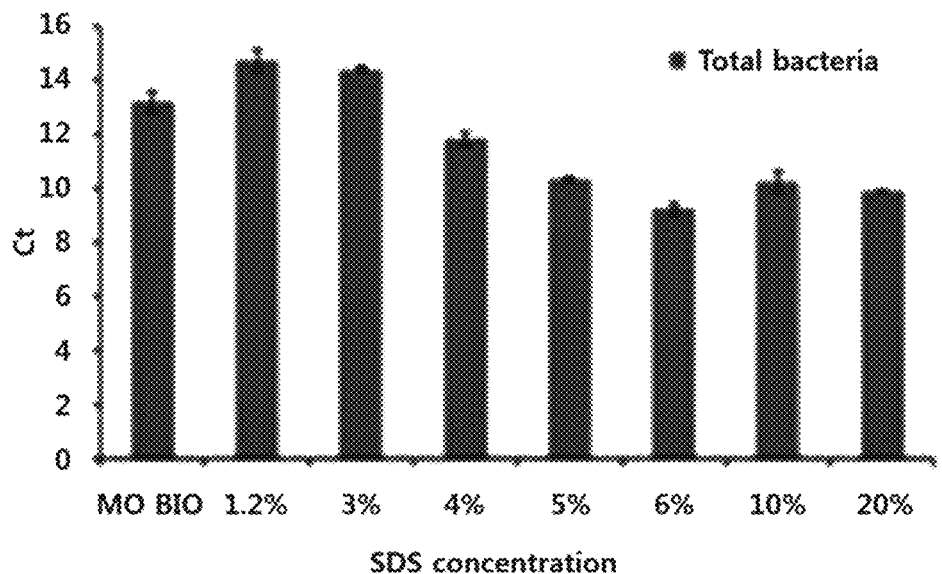
FIGS. 1A-1D illustrate the total bacteria recovery (FIG. 1A), the bacteria recovery rate (FIG. 1B), the nucleic acid recovery rate (FIG. 1C), and the stool separation (FIG. 1D) according to the concentration of the surfactant.

An aspect of the present invention provides a method for extracting nucleic acids from a biological sample, the method including: (a) disrupting a biological sample by bead-beating a biological sample-bead solution prepared by adding a buffer solution, a surfactant, and beads to the biological sample; (b) purifying a biological sample-bead solution in which the biological sample is disrupted; (c) performing a repurification by adding a kosmotropic salt solution to the purified solution; and (d) extracting nucleic acids from the repurified solution.

Hereinafter, the present invention will be described in more detail.

The inventors of the present invention revealed during the study and development of a method for extracting nucleic acids from a biological sample that when a surfactant and a kosmotropic salt solution are added to disrupting the biological sample and purifying the biological sample, respectively, the total bacteria recovery, the bacteria recovery rate, and the nucleic acid recovery rate are improved by lifting up impurities to the upper part instead of precipitating the impurities, such that pathogens can be detected more sensitively and accurately, thereby completing the present invention.

An aspect of the present invention provides a method for extracting nucleic acids from a biological sample, the method including: (a) disrupting a biological sample by bead-beating a biological sample-bead solution prepared by adding a buffer solution, a surfactant, and beads to the biological sample; (b) purifying a biological sample-bead solution in which the biological sample is disrupted; (c) performing a repurification by adding a kosmotropic salt solution to the purified solution; and (d) extracting nucleic acids from the repurified solution.

The term "biological sample" used in the present specification refers to not only samples that are obtainable from an organism, but also all the samples that have room for containing nucleic acids. Specifically, examples of the biological sample include human and animal blood, plant body fluids, human and animal waste, microbial culture liquid, cell culture liquid, virus culture liquid, biopsy culture liquid, soil, air, and the like, and preferably include stool, blood, and soil, but are not limited thereto.

The term "buffer solution" used in the present specification is not particularly limited in type, and examples thereof may include a tris buffer solution, a sodium phosphate buffer solution or a potassium phosphate buffer solution, but are not limited thereto. The buffer solution is preferably a tris-hydrochloric acid (tris-HCl) solution, and more preferably, a 5 to 15 mM tris-hydrochloric acid solution.

The term "surfactant" used in the present specification may be an anionic surfactant, a cationic surfactant, an amphoteric surfactant or a non-ionic surfactant, but is more preferably an anionic surfactant. The anionic surfactant may be any one selected from the group consisting of, for example, sodium dodecyl sulfate (SDS), sodium octylbenzene sulfonate (NaOBS), sodium dodecylbenzene sulfate (SDBS), sodium dodecyl sulfonate (SDSA), sodium dodecyl benzene sulfonate, sodium butylbenzoate (NaBBS), ammonium lauryl sulfate, sodium deoxycholate, sodium lauryl ether sulfate (SLES), sodium myreth sulfate (SMES), dioctyl sodium sulfosuccinate, perfluorooctane sulfonate (PFOS), perfluorobutane sulfonate, sodium stearate, sodium lauroyl sarcosinate, perfluoronanoate, perfluorooctanate (PFOA or PFO), and combinations thereof, but is not limited thereto, and is preferably sodium dodecyl sulfate. The reason for adding the surfactant in the present invention is to be able to increase the effect of destroying a target material in the sample and to prevent impurities from inhibiting nucleic acid separation. In the present invention, the surfactant may be present in an amount of 1 to 20% (v/v) based on the total weight of the biological sample, but when the content thereof is less than 1% or more than 20%, the nucleic acid recovery rate may be inhibited.

The term "bead-beating" used in the present specification refers to a method for disrupting a solid material in a sample by physical force, and is carried out by shaking a sample solution containing beads by hand or using an automatic vibrator. In the present invention, a method for vibrating the beads by an automatic vibration method was used. There is no limitation in a material for the "bead", but preferably, glass beads may be used. As the diameter of the beads, beads or mixtures thereof with a size of 0.03 to 2 mm, preferably, 0.1 mm to 0.5 mm are preferred, but the beads are not limited thereto. The amount of beads contained in the sample solution is preferably 10 to 200 mg, and may be more preferably 1 to 25 wt % of the biological sample-bead solution. In the present invention, the biological sample may be disrupted by bead-beating the biological sample-bead solution under a condition of 10 to 80 Hz, but the present invention is not limited thereto. The bead-beating is carried out preferably for 3 to 10 minutes, but is not limited thereto.

The purification step in the present specification means a process of primarily separating impurities having a large particle size from a liquid material containing nucleic acids, and may be carried out through centrifugation or filtration. In the case of purification through centrifugation, preferably, the disrupted biological sample-bead solution may be centrifuged at 6,000 to 9,000 rpm for 30 to 90 seconds to separate only the supernatant thereof from the solid impurities, but the purification method is not limited thereto.

The repurification step of the present specification means a process of secondarily separating impurities having a small particle size by adding a kosmotropic salt solution to the purified solution, and lifting up the impurities to the upper part of a liquid material containing nucleic acids, and may be carried out through centrifugation or a heat treatment.

The term "kosmotropic salt" used in the present specification means a salt consisting of $SO_4^{2-}$, $HPO_4^{2-}$, $OH^-$, $F^-$, $HCOO^-$, $CH_3COO^-$ or $Cl^-$ and a cation. However, when bonded to the kosmotropic anion, $Mg^{2+}$ as the cation has exceptionally no kosmotropic characteristics, so that $Mg^{2+}$ is excluded. The cation may be $NH_{4+}$, $Rb^+$, $K^+$, $Na^+$, $Cs^+$, $Li^+$, $Ca^{2+}$, or $Ba^{2+}$. The kosmotropic salt may be preferably sodium sulfate ($Na_2SO_4$), sodium chloride (NaCl), ammonium sulfate (($NH_4)_2SO_4$), or sodium acetate (NaOAc), but is not limited thereto, and sodium sulfate is most preferred. The concentration of the sodium sulfate solution is preferably 1.0 to 5.0 M, but is not limited thereto. The reason for adding the kosmotropic salt solution is to separate nucleic acids and impurities. After the kosmotropic salt solution is added, impurities separated into the upper part may be removed once more by centrifuging or heat-treating the mixture. The centrifugation may be carried out by centrifuging the mixture at 6,000 to 9,000 rpm for 30 to 90 seconds, but is not limited thereto. The heat treatment may be carried out at 50 to 90° C., but is not limited thereto.

The term "nucleic acid extraction" used in the present specification may be carried out by a method publicly known in the art, and specifically, see the document U.S. Pat. No. 5,234,809.

The purification step and the repurification step may be carried out by arbitrarily selecting the disclosed method. Preferably, i) both the purification step and the repurification step may be carried out through centrifugation, or ii) the purification step may be carried out through filtration and the repurification step may be carried out through a heat treatment. In particular, the method in i) is suitable for applying to a device automation method when the method in ii) is used for a kit method.

Hereinafter, the present invention will be described in more detail with reference to the following Examples. However, the present invention is not limited by the Examples.

EXAMPLES

Example 1

Separation and Purification of Stool Sample

400 μl of a 10 mM tris-hydrochloric acid (pH 8 or more) as a buffer solution and sodium dodecyl sulfate (SDS, AMRESCO) as a surfactant were added to 200 mg of a stool sample so as to be a concentration of 6% (v/v) based on the buffer solution volume, 0.4 g of glass beads with a size of 100 μm (DAIHAN Scientific Co., Ltd.) was put into the mixture in order to disrupt the stool sample and a target to be tested and measured, and then bead-beating (Scientific Industries) was carried out under a condition of 50 Hz for 5 minutes. Thereafter, centrifugation (LABOGENE) was carried out at 8,000 rpm for 1 minute, the supernatant was transferred to a tube, a 2.5 M sodium sulfate ($Na_2SO_4$, Sigma-Aldrich) solution was added to the separated supernatant, the resulting mixture was stirred so as to be uniformly mixed, and then centrifugation was carried out again at 8,000 rpm for 1 minute. 1 minute later, when impurities were lifted at the top of the liquid, only the solution at the bottom was transferred to a new tube. Nucleic acids were extracted from the transferred solution by using the Boom technology (see the document [US005234809A]).

Example 2

Identification of Bacteria and Nucleic Acid Recovery Rates from Stool Sample According to Concentration of Surfactant 2.1. Separation and Purification of Stool Sample by Varying Concentration of Surfactant In order to identify the bacteria and nucleic acid recovery rates according to the concentration of SDS from a stool sample, the entire process as in Example 1 was carried out, except that DNA of salmonella (ATCC) prepared at a concentration of $10^6$ cfu/ml or *Staphylococcus aureus* (ATCC) extracted at a concentration of $10^6$ cfu/ml was added to 200 mg of the stool sample, and the SDS was added such that each concentration thereof became 1.2%, 3%, 4%, 5%, 6%, 10%, and 20% based on the buffer solution volume (see FIG. 1D).

2.2. Measurement of Total Bacteria Amount, Bacteria Recovery Rate, and Nucleic Acid Recovery Rate from Separated Sample Nucleic acids were extracted by using the Boom technology, the amounts of the separated nucleic acids were compared by carrying out a polymerase chain reaction (PCR) using a universal bacteria primer in order to measure the total bacteria amount, and the bacteria and nucleic acid recovery rates were calculated by using the equation (the concentration of the extracted bacteria or nucleic acids)/(the concentration of the initially added bacteria or nucleic acid)*100(%)).

Figure 1B:
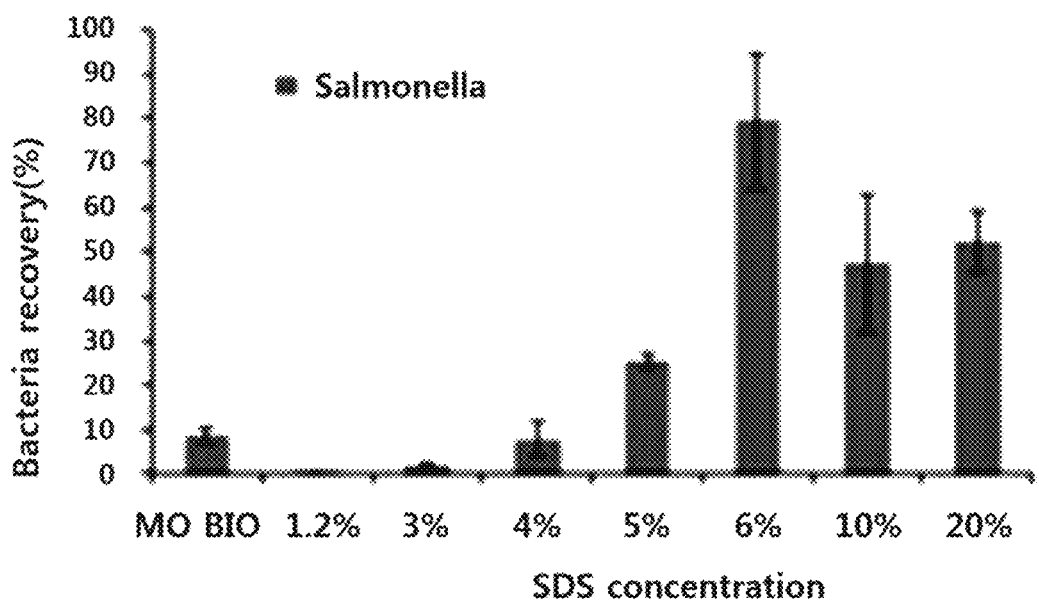
Figure 1C:
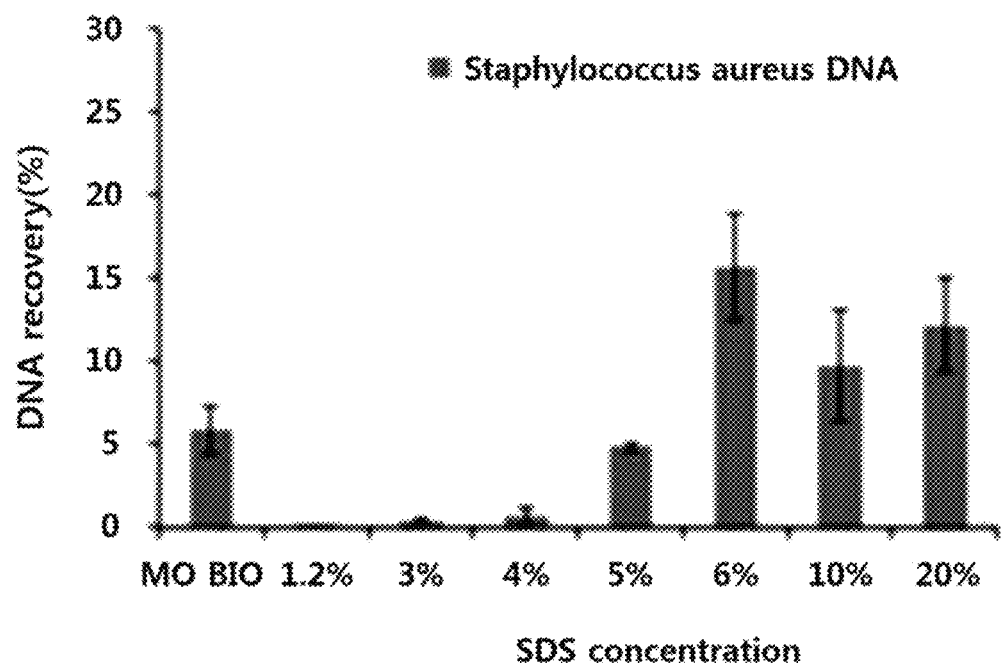
Figure 1D:
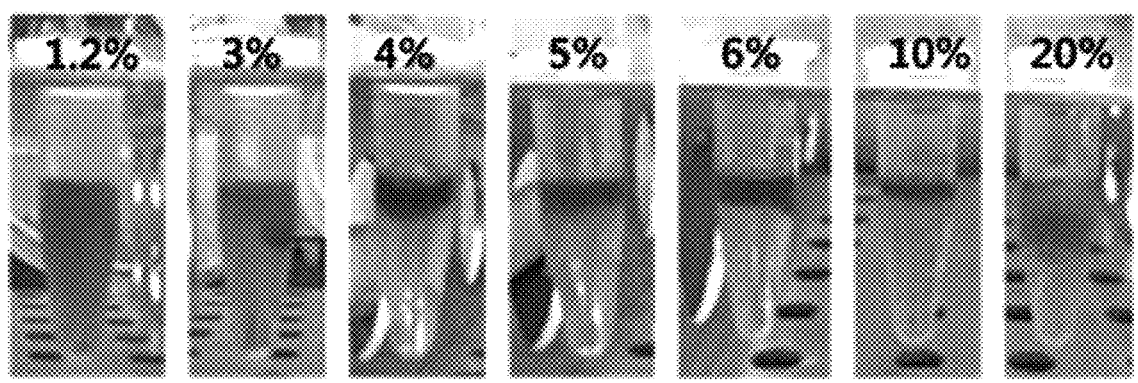

As a result of the experiment, in the case where the SDS was added at a concentration of 6%, the measurement of the total bacteria amount (see FIG. 1A), the bacteria recovery rate (see FIG. 1B, and the nucleic acid recovery rate (see FIG. 1C) exhibited the best results. Further, even when the sample was compared with a kit sold by MO BIO Laboratories, which is most frequently used in extracting stool samples, it was confirmed that the highest recovery rate was measured when the SDS of 6% based on the total buffer solution volume was used.

Example 3

Identification of Bacteria Recovery Amount from Stool Sample According to Concentration of Sodium Sulfate Solution 3.1. Separation and Purification of Stool Sample by Varying Concentration of Sodium Sulfate Solution In order to identify the concentration of a sodium sulfate ($Na_2SO_4$) solution at which nucleic acids could be extracted while effectively separating the stool sample, the entire process as in Example 1 was carried out, except that the sodium sulfate solution was added thereto by varying the concentration (0.25 M (0.1×), 1.25 M (0.5×), and 2.5 M (1×)) of the sodium sulfate solution (see FIG. 2B).

3.2. Measurement of Total Bacteria Amount from Separated Sample

Figure 2A:
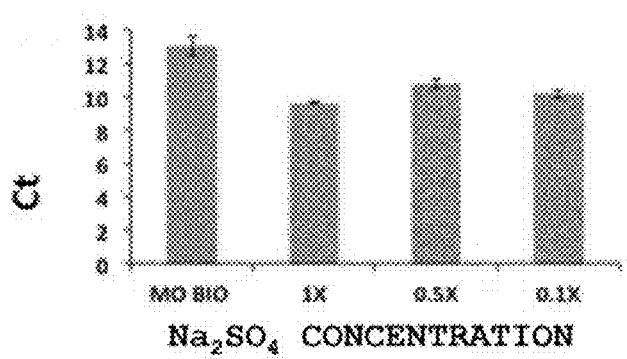
FIGS. 2A-2B illustrate the total bacteria recovery (FIG. 2A) and the stool separation (FIG. 2B) according to the concentration of sodium sulfate ($Na_2SO_4$).
Figure 2B:
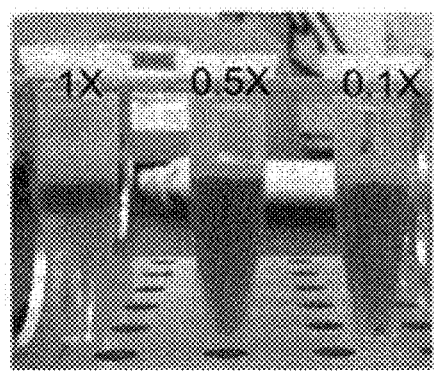

As a result of measuring the total bacteria recovery amount by the method described in Example 2.2, the highest total bacteria recovery amount was exhibited when a sodium sulfate solution at 2.5 M (final concentration 0.7 M) was used (see FIG. 2A), and only the case where the concentration was 2.5 M exhibited a result that the stool sample was lifted up to the top of the solution (see FIG. 2B).

Example 4

Identification of Nucleic Acid Extraction Amount According to Heat Treatment

In order to confirm whether the stool sample before the purification step needs a heat treatment, the nucleic acid extraction amount was identified by carrying out the entire process as in Examples 1 and 2, except that the heat treatment was carried out under a condition of 40° C. (where the lid does not open by itself) for each time (not treated, 5 minutes, 10 minutes, and 20 minutes).

As a result of the experiment, unlike a kit manufactured by Qiagen, Inc. among currently commercialized kits where nucleic acid extraction was carried out by heat-treating the stool sample during the process of separating stool, it was confirmed that in an experimental result where the stool sample was not heat-treated (0 minute), the high nucleic acid extraction amount, the high bacteria recovery rate, and the high DNA recovery rate were measured (see FIGS. 3A to 3C).

Example 5

Identification of Nucleic Acid Extraction Amount According to Intensity of Centrifugation In order to identify the effective intensity of centrifugation for separating a stool sample, the entire process as in Examples 1 and 2 was carried out, except that the intensity for carrying out the centrifugation was changed into conditions of 2,000 rpm, 4,000 rpm, 6,000 rpm, and 8,000 rpm.

As a result of the experiment, when the centrifugation was carried out by setting the intensity of the centrifugation to the condition of 8,000 rpm, it was confirmed that the lowest threshold of cycle (Ct) value was exhibited (see FIG. 4A), and the largest amount of nucleic acids was present.

Example 6

Identification of Bacteria and Nucleic Acid Recovery Rates According to Type of Target Sample In order to identify the bacteria and nucleic acid recovery rates according to the stool of a dog and the stool of a human, the same result contents were measured by the kit manufactured by MO BIO Laboratories, which is most frequently used regardless of the type of sample, while the same experiment as in Examples 1 and 2 was carried out on each sample.

As a result of the experiment, it was confirmed that when the experimental result was compared to the kit manufactured by MO BIO Laboratories, the excellent performance was exhibited in terms of all of the total bacteria recovery amount, the bacteria recovery rate, and the nucleic acid recovery rate.

Example 7

Identification of Bacteria and Nucleic Acid Recovery Rates According to Amount of Sample A currently commercialized kit requires that about 200 to 250 mg of a sample is used, but in order to confirm that nucleic acids can be extracted even from a sample in a less amount, the total bacteria recovery amounts, the bacteria recovery rates, and the nucleic acid recovery rates were compared by performing the entire process as in Examples 1 and 2, except that the amounts of two samples of dog stool and human stool were varied, that is, 10 mg (10 mg of stool+190 μl of distilled water), 20 mg (20 mg+180 μl of distilled water), 50 mg (50 mg of stool+150 μl of distilled water), 100 mg (100 mg of stool+100 μl of distilled water), 150 mg (150 mg of stool+50 μl of distilled water), 200 mg (200 mg of stool), and 250 mg (250 mg of stool) of samples were used.

As a result of the experiment, in the case where 50 mg or more of the dog stool sample and 100 mg or more of the human stool sample were included, impurities could be separated, which shows that nucleic acids can be detected only in an amount of the sample, which is significantly lower than the amount of a sample required by a commercially available kit sold in the related art, and confirms that excellent performance was exhibited regardless of the amount of stool (see FIG. 6).

Example 8

Observation of Separation and Purification of Blood Sample

It was confirmed that impurities were removed by also applying the method used for the separation of the stool sample to a blood (whole blood) sample which is one of the complex samples. Since the amount of the blood sample recommended by a commercialized kit is 200 µl, the experiment was performed based on a volume of the sample, which is 200 µl.

By using the whole blood of a human, 20 µl (20 µl of whole blood+180 µl of distilled water), 50 µl (50 µl of whole blood+150 µl of distilled water), 100 µl (100 µl of whole blood+100 µl of distilled water), and 200 µl (200 µl of whole blood) were each prepared. Impurities were separated and purified from the prepared samples by the method described in Example 1. As a result of the experiment, it was confirmed that impurities were separated and purified from the sample containing 100 µl or more of whole blood (see FIG. 7A).

The nucleic acid recovery rate was identified by using the method described in Example 2 using 100 µl of a blood sample. As a result of the experiment, adenovirus exhibited a recovery rate of 70% as compared to the DNA mini kit manufactured by Qiagen, Inc., and Gram positive bacteria exhibited a recovery rate of about 40 times higher than the DNA mini kit manufactured by Qiagen, Inc. (see FIG. 7B).

Example 9

Observation of Separation and Purification of Soil Sample

It was confirmed that impurities were removed by applying the method used for the separation of the stool sample to a soil sample which is one of the other complex samples. First, a sample in which 100 µl of distilled water was added to 250 mg of each of two soil samples collected from different places was prepared, and impurities were separated and purified by the method described in Example 1. As a result of the experiment, it was confirmed that impurities were separated and purified from both the two types of soil (see FIG. 8A).

The nucleic acid recovery rate was identified by using the method described in Example 2 using 250 mg of a soil sample. As a result of the experiment, both the two soil samples exhibited a recovery rate by about 2 times for *Staphylococcus aureus*, which is one of the Gram positive bacteria, based on the kit manufactured MO BIO Laboratories (see FIG. 8B).

Example 10

Identification of Nucleic Acid Extraction from Stool Sample According to Size of Bead In order to identify the nucleic acid extraction rate from the stool sample according to various bead sizes in the disrupting of the stool sample using glass beads, an experiment was carried out as follows.

Figure 9A:
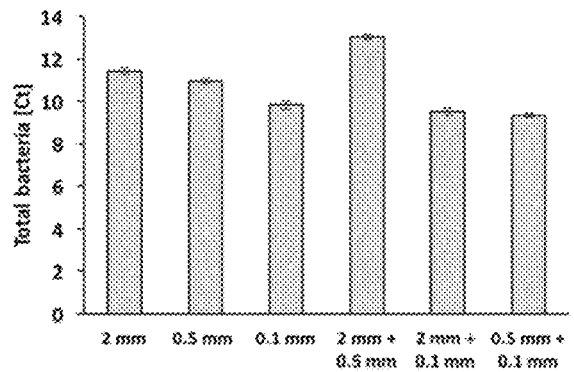
FIGS. 9A-9B illustrate the nucleic acid extraction rates from stool samples according to various bead sizes (FIG. 9A), and *Staphylococcus aureus* nucleic acid recovery rate according to various bead sizes (FIG. 9B).
Figure 9B:
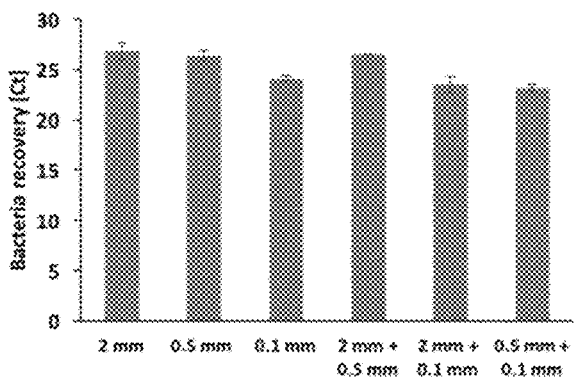

Beads having a diameter of 2 mm, 0.5 mm, and 0.1 mm and 2 mm+0.5 mm, 2 mm+0.1 mm, and 0.5 mm+0.1 mm mixtures of these beads were added in an equal amount, stool samples into which *Staphylococcus aureus* was put into at the same concentration were disrupted, and then the nucleic acid extraction rate and the nucleic acid recovery rate of *Staphylococcus aureus* present in the stool were identified (see FIG. 9).

As a result of the experiment, it could be confirmed that a part of the stool was not disrupted well from the beads having a diameter of 2 mm, showing a lower efficiency than the beads having different sizes even for the nucleic acid extraction rate. Therefore, it was confirmed that the beads exhibiting excellent nucleic acid recovery efficiency were beads having a size of 0.1 mm to 0.5 mm in diameter or mixtures thereof.

Example 11

Identification of Nucleic Acid Extraction by Filtration and Heat Treatment 11.1. Purification of Sample by Filtration In the existing method for separating a complex sample, a first purification process using centrifugation performed after disrupting a stool sample and a complex sample may be carried out by using a non-centrifugation method. In order to confirm whether the first purification process may be replaced with filtration, an experiment was carried out as follows.

An experiment was carried out in the same manner as in Example 1, except that a method of using filtration was used instead of the centrifugation in Example 1. After the stool sample and complex sample targets were disrupted by the method described in Example 1, a primarily purified solution was obtained by passing the disrupted sample targets through an object having a space through which beads and large impurities could not escape. The purified solution was subjected to a repurification process by using the existing centrifugation, and nucleic acids were recovered from the repurified solution.

Figure 10:
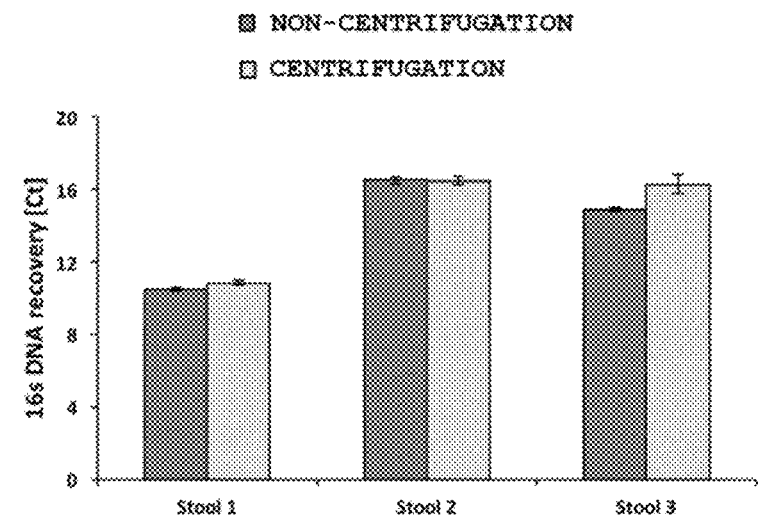
FIG. 10 illustrates the separation and purification results of stool samples using filtration and centrifugation.

As a result of carrying out the experiment by using stool samples having three different shapes and forms, it was confirmed that this process was a replaceable process because this process did not exhibit a significant difference in terms of a nucleic acid recovery rate as compared to the centrifugation method (see FIG. 10).

11.2. Repurification of Sample by Heat

In the method for separating a complex sample, repurification is performed by using centrifugation, but impurities were repurified by carrying out a heat treatment without using centrifugation.

200 mg of a stool sample, a buffer with a pH of 8 or more, a 6% (v/v) surfactant SDS, and 0.4 g of glass beads having a size of 70 to 100 µm for destroying the stool sample and the measurement target were put into a tube, and bead-beating was carried out for 5 minutes. Thereafter, a solution excluding large impurities and glass beads was transferred to a new tube by using centrifugation, a 2.5 M $Na_2SO_4$ solution was added thereto, a heat treatment was carried out at each of 45° C., 55° C., 65° C., 75° C., 85° C., and 95° C. for 5 minutes or 10 minutes, and then the results were observed in comparison with the result obtained by performing repurification using centrifugation. Further, nucleic acid extraction concentrations (total bacteria) were measured by carrying out the PCR on the stool samples treated at the temperatures for 10 minutes, and the results were compared with those of the samples by centrifugation.

Figure 11A:
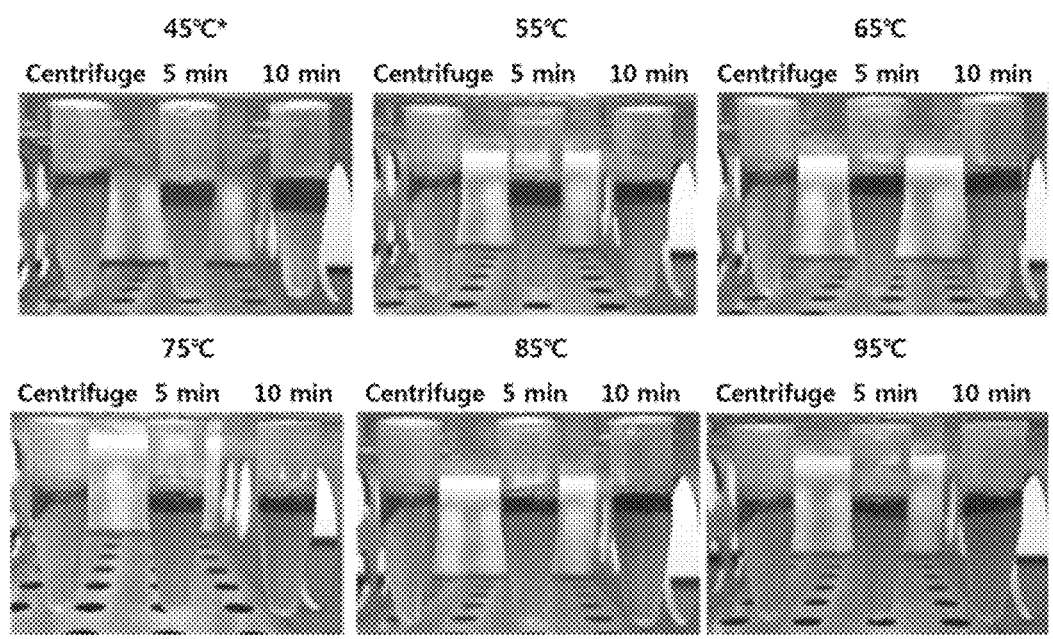
FIGS. 11A-11C illustrate the repurification results of the stool samples through a heat treatment (FIG. 11A), the repurification results of the blood samples (FIG. 11B), and the nucleic acid recovery rates in the stool samples (FIG. 11C).
Figure 11B:
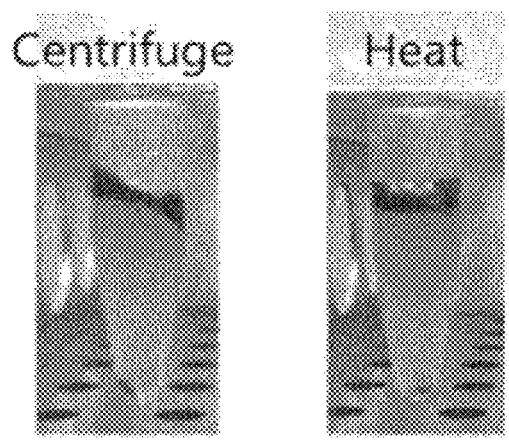
Figure 11C:
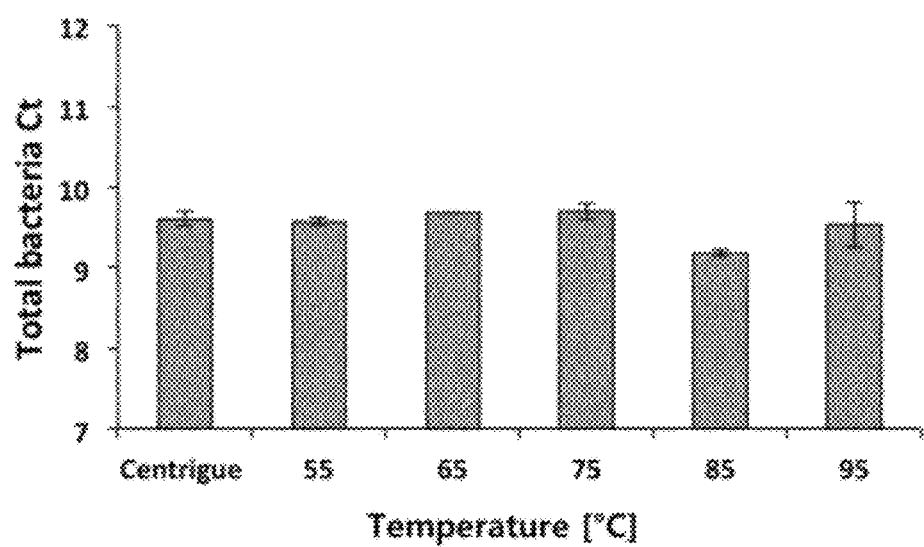

As a result of the experiment, it could be confirmed that stool was successfully separated even under various temperature conditions, and the difference did not exhibit a significant difference from that by centrifugation (see FIG. 11A). As a result of applying the same method to a blood sample, it was confirmed that impurities were successfully separated by the heat treatment instead of centrifugation (see FIG. 11B). In addition, as a result of carrying out the PCR on the stool sample, it was confirmed that a Ct value similar to that of the centrifugation was exhibited at all the temperatures without any effect of the temperature (see FIG. 11C).

11.3. Separation and Purification of Stool Sample by Filtration and Heat Treatment An experiment was carried out in the same manner as in Example 1, except that for the stool having three different shapes and forms, filtration and a heat treatment were used instead of the primary centrifugation and the secondary centrifugation in Example 1, respectively.

Figure 12:
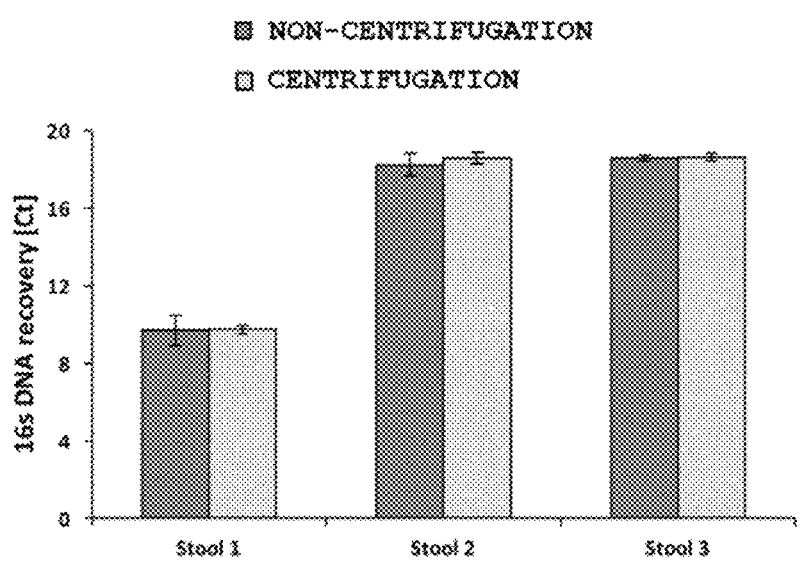
FIG. 12 illustrates the separation and purification results of the stool samples using a non-centrifugation method in which the purification step and the repurification step are carried out through filtration and a heat treatment, respectively.

As a result of the experiment, it was confirmed that the experiment exhibited a result similar to that of the purification and repurification steps all using the centrifugation, and therefore, it was confirmed that the complex sample could be separated and purified by using the non-centrifugation (see FIG. 12).

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is represented by the claims to be described below rather than the foregoing detailed description, and it should be interpreted that the meaning and scope of the claims and all the changes or modified forms derived from the equivalent concepts thereto fall within the scope of the present invention.

Example 12

Observation of Separation and Purification of Chicken Manure Sample

Figure 13A:
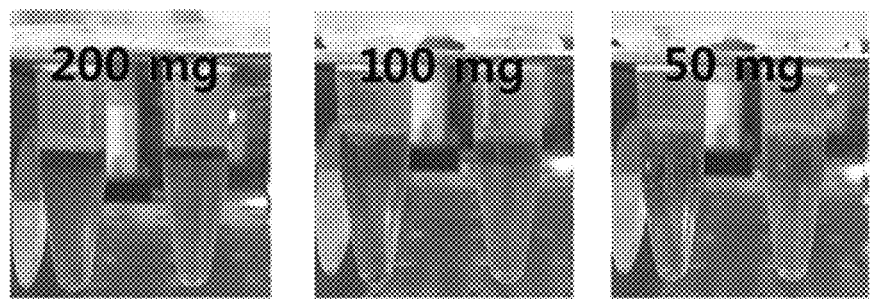
FIGS. 13A-13C illustrate the separation and purification results of various amounts of chicken manure samples (FIG. 13A) and the nucleic acid (FIG. 13B) and RNA virus (FIG. 13C) recovery rates from the chicken manure samples.

Considering that manure samples of poultry (chickens, ducks, and the like) or wild birds are used when confirming avian influenza frequently occurring every year, it was confirmed that impurities were removed by ahead described applying the method used for preparing the stool sample derived from the human to a chicken manure sample. First, DNA extracted from adenovirus(high concentration: 105 pfu/mL, low concentration: 103 pfu/mL) and influenza virus (H1N1 virus)(high concentration: 106 pfu/mL, low concentration: 102 pfu/mL) at two prepared concentrations were put into various amounts (200 mg, 100 mg, and 50 mg) of chicken manure samples collected from chicken, and then the entire process as in Example 1 was carried out. As a result of the experiment, all the various amounts of chicken manure samples were confirmed purified with impurities removed (see FIG. 13A).

Figure 13B:
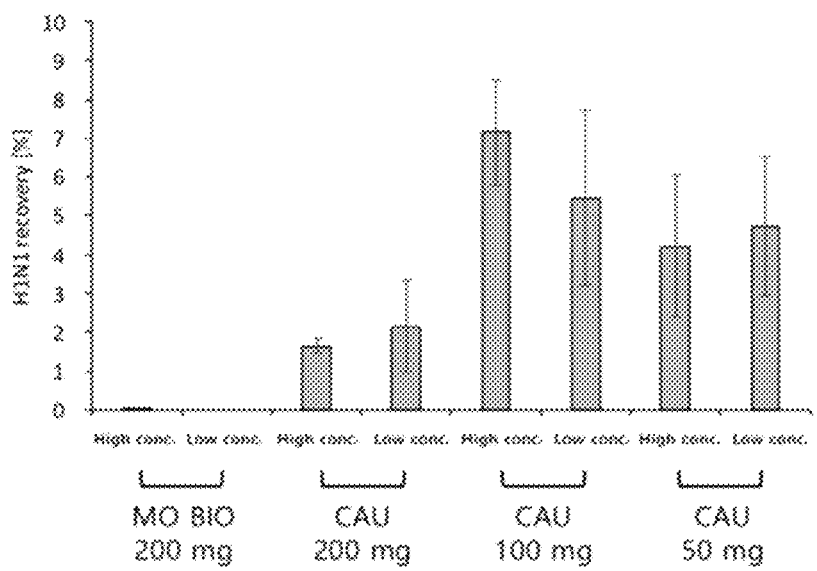
Figure 13C:
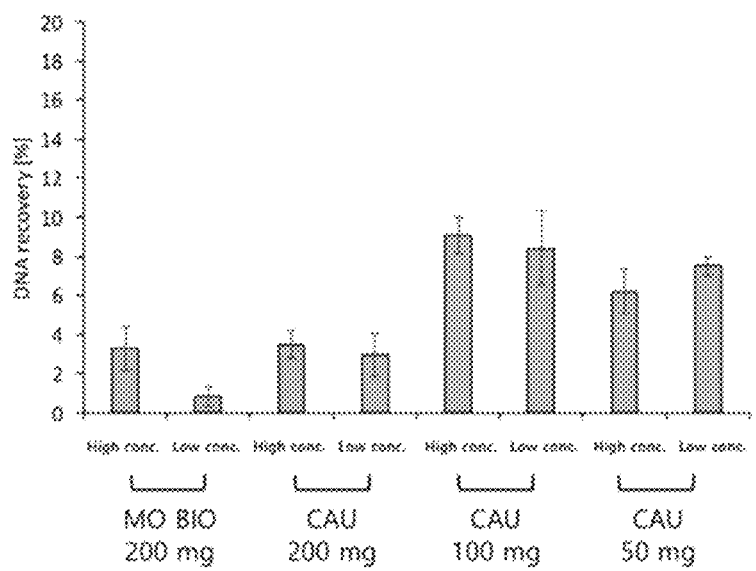

The adenovirus DNA and influenza virus recovery rates were identified by using the method described in Example 1. As a result of the experiment, the chicken manure samples exhibited virus recovery rates to or 2 to 3 times in that of adenovirus obtained by use of the kit of MO BIO Laboratories (see FIG. 13B). The chicken manure samples exhibited virus recovery rates to or 2 to 3 times in that of influenza virus obtained by use of the kit of MO BIO Laboratories (see FIG. 13C).

What is claimed is:

1. A method for extracting nucleic acids from a biological sample, the method comprising:
   (a) disrupting a biological sample by bead-beating a biological sample-bead solution prepared by adding a buffer solution, a surfactant, and beads to the biological sample, wherein the biological sample-bead solution is not subject to heat treatment;
   (b) centrifuging the biological sample-bead solution in which the biological sample has been disrupted, thereby forming a supernatant and solid impurities;
   (c) separating the supernatant from the solid impurities by transferring the supernatant to a first vessel;
   (d) adding a 1.25 to 2.5 M sodium sulfate ($Na_2SO_4$) solution to the supernatant and mixing, thereby forming a treated supernatant;
   (e) centrifuging or heat-treating the treated supernatant to form a top portion of the centrifuged or heat-treated supernatant comprising impurities and a liquid bottom portion of the centrifuged or heat-treated supernatant;
   (f) separating the top portion of the centrifuged or heat-treated supernatant from the liquid bottom portion of the centrifuged or heat-treated supernatant by transferring the liquid bottom portion to a second vessel, thereby forming a repurified solution consisting of the liquid bottom portion; and
   (g) extracting nucleic acids from the repurified solution.

2. The method of claim 1, wherein the surfactant is an anionic surfactant.

3. The method of claim 1, wherein the surfactant is present in an amount of 1 to 20% (v/v) based on a total weight of the biological sample.

4. The method of claim 3, wherein the disrupting of the biological sample by bead-beating the biological sample-bead solution comprises vibrating the beads by automatic vibration having a frequency of 10 to 80 Hz.

5. The method of claim 1, wherein the treated supernatant is heat-treated.

6. The method of claim 5, wherein the heat-treating is carried out at 50 to 90° C.

7. The method of claim 1, wherein the biological sample is any one selected from the group consisting of stool, blood, and soil.

8. The method of claim 1, wherein in step (a), the biological sample-bead solution is bead-beaten by vibrating the beads by automatic vibration having a frequency of 10 to 50 Hz for a period of 3 to 10 minutes.

9. The method of claim 8, wherein the period is 3 to 5 minutes.

10. A method for extracting nucleic acids from a biological sample, the method comprising:
    (a) disrupting a biological sample by bead-beating a biological sample-bead solution prepared by adding a buffer solution, a surfactant, and beads to the biological sample, wherein the biological sample-bead solution is not subject to heat treatment;
    (b) filtering the biological sample-bead solution in which the biological sample has been disrupted, by passing the disrupted biological sample-bead solution through an object having a space through which the beads and impurities cannot escape, thereby forming a filtrate and a filtered material comprising said beads and said impurities;

(c) separating the filtrate from the filtered material by transferring the filtrate to a first vessel;
(d) adding a 1.25 to 2.5 M sodium sulfate ($Na_2SO_4$) solution to the filtrate and mixing, thereby forming a treated filtrate;
(e) performing a heat treatment on the treated filtrate to lift impurities;
(f) separating the lifted impurities from the treated filtrate without the impurities by transferring the treated filtrate without the impurities to a second vessel, thereby forming a repurified solution consisting of the treated filtrate without the impurities; and
(g) extracting nucleic acids from the repurified solution, wherein the biological sample is any one selected from the group consisting of stool, blood, and soil.

* * * * *